United States Patent [19]
Venturini

[11] Patent Number: 5,112,316
[45] Date of Patent: May 12, 1992

[54] DISPOSABLE SAFETY SYRINGE

[76] Inventor: Aldo Venturini, Via Orbetello N. 176, I-10148 Turin, Italy

[21] Appl. No.: 370,866

[22] Filed: Jun. 23, 1989

[30] Foreign Application Priority Data

Jun. 23, 1988 [IT] Italy ............................... 67588 A/88

[51] Int. Cl.⁵ .............................................. A61M 5/00
[52] U.S. Cl. ........................... 604/195; 604/198; 604/263
[58] Field of Search ............... 604/195, 198, 187, 263, 604/229, 110, 111

[56] References Cited

U.S. PATENT DOCUMENTS

| | | | |
|---|---|---|---|
| 4,300,678 | 11/1981 | Gyure et al. | 604/111 |
| 4,664,128 | 5/1987 | Lee | 604/187 X |
| 4,675,005 | 6/1987 | Deluccia | 604/110 |
| 4,747,829 | 5/1988 | Jacob et al. | 604/110 |
| 4,747,830 | 5/1988 | Gloyer et al. | 604/195 X |
| 4,838,869 | 6/1989 | Allard | 604/195 |
| 4,874,382 | 10/1989 | Lindemann et al. | 604/195 |

Primary Examiner—John D. Yasko
Attorney, Agent, or Firm—Keil & Weinkauf

[57] ABSTRACT

According to the invention, the disposable safety syringe comprises means (18) for retaining the empty needle (17) in a use position, which means are disengageably actable upon a bushing (16) for mounting a needle, the which bushing is retractably inserted into the needle-holder head (12) of the syringe body (11); means (13.4/16.5) for the inseparable coupling between the bushing (16) and the plunger (13) of the syringe, achieving this coupling at the end of the stage for injecting the liquid contained in the syringe body; means (10) for disengaging the retaining means (18) from the bushing (16), driven by the plunger and achieving disengagement at the end of the stage for injecting the liquid contained in the syringe body, substantially in step with the action for inseparable coupling between bushing (16) and plunger (13), in addition to means (10.1) for automatically returning the plunger to a retracted position within this syringe body at the end of the stage for injecting the liquid contained in the syringe body, functioning automatically upon cessation of the manual action exerted on the plunger, in such a way that the plunger is automatically retracted into the syringe body, and in a manner integral to and inseparable from the plunger, the empty needle and its mounting bushing are likewise automatically retracted into a safety position in the syringe body (FIG. 1).

26 Claims, 6 Drawing Sheets

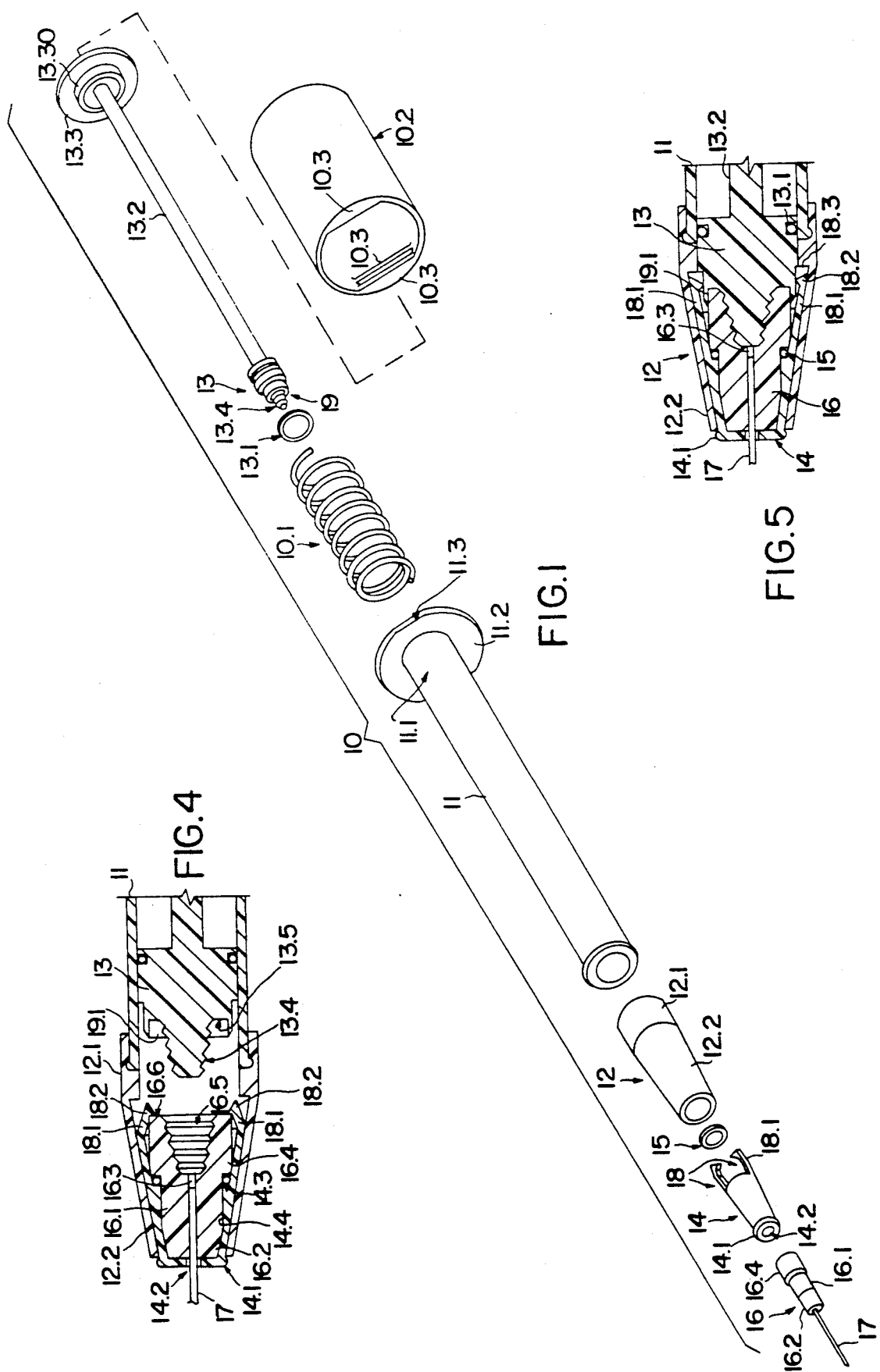

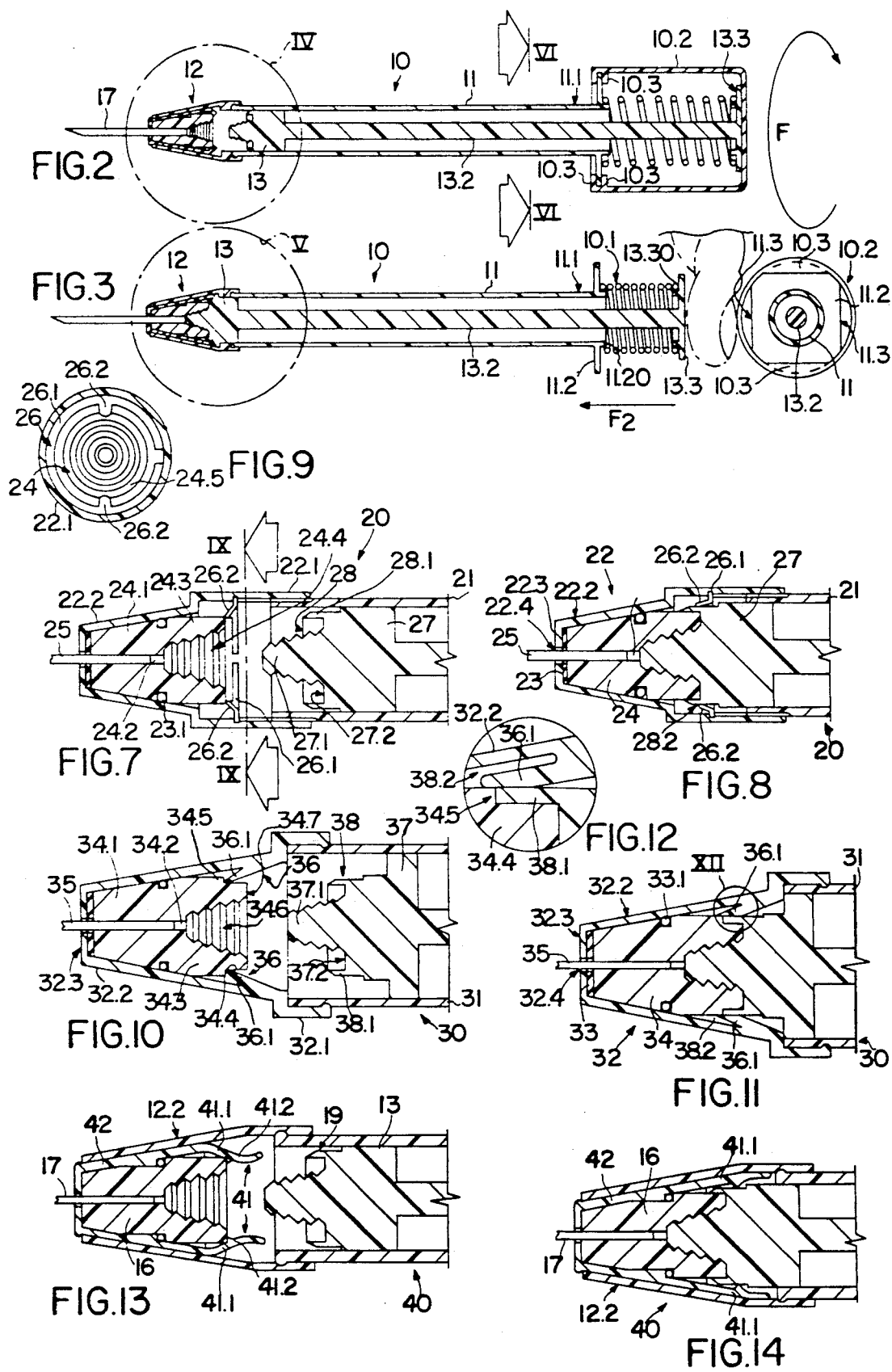

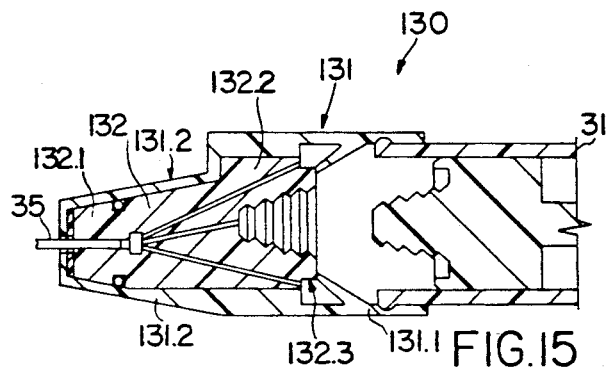
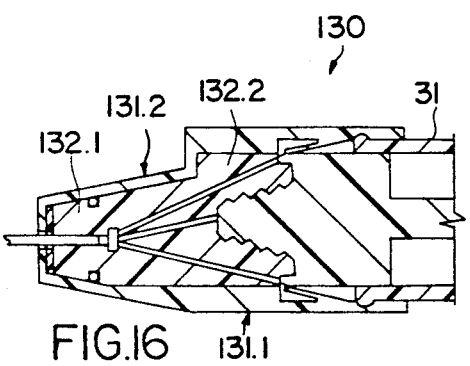
FIG.15  FIG.16
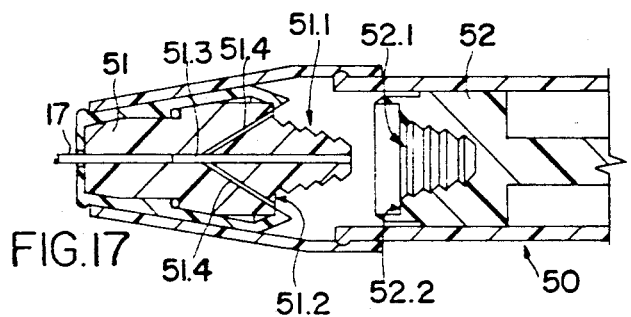
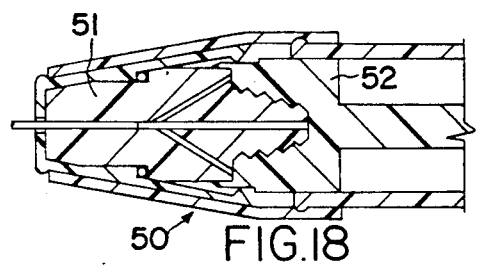
FIG.17  FIG.18
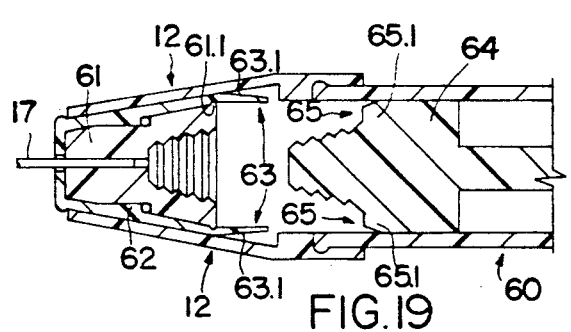
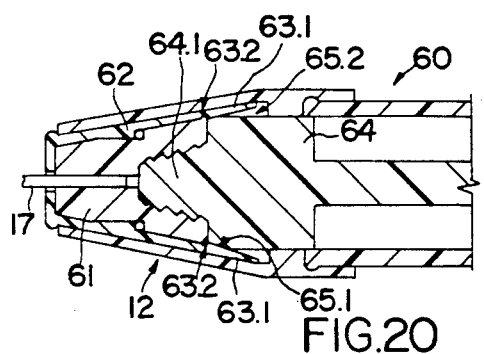
FIG.19  FIG.20
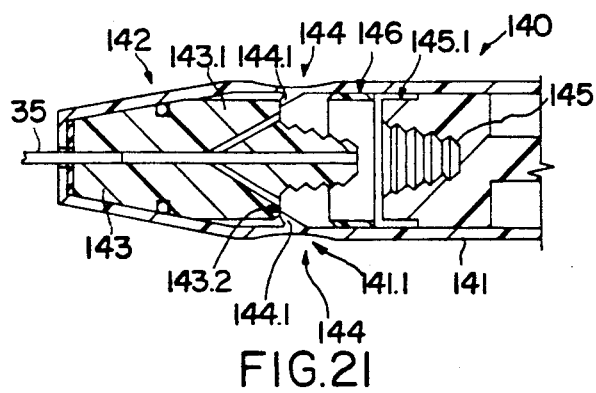
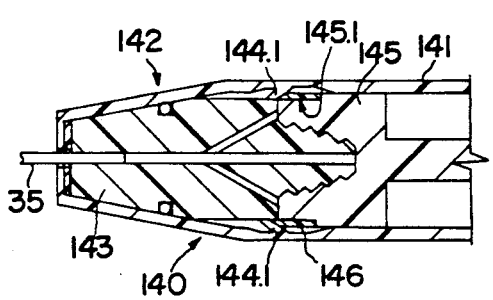
FIG.21  FIG.22

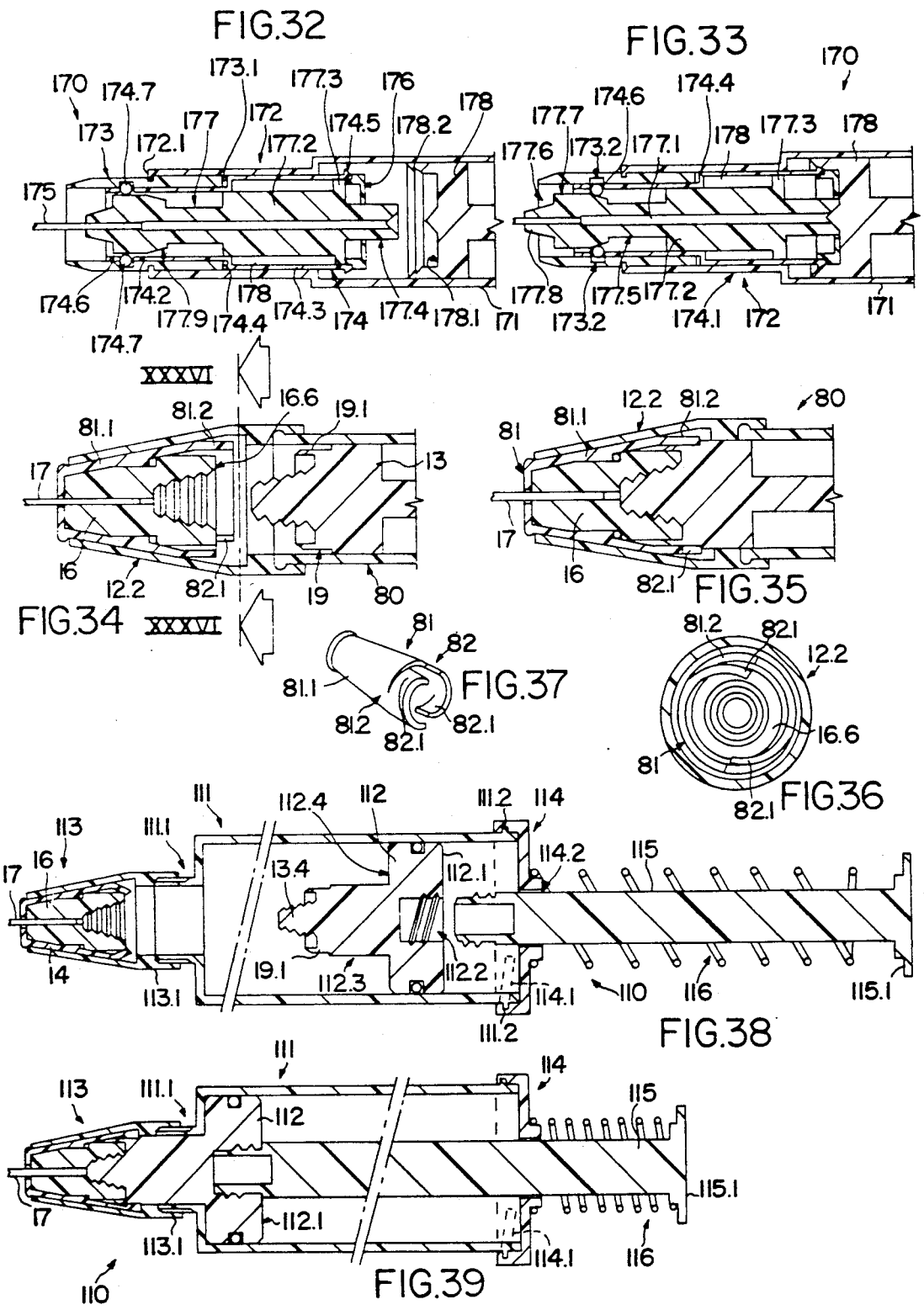

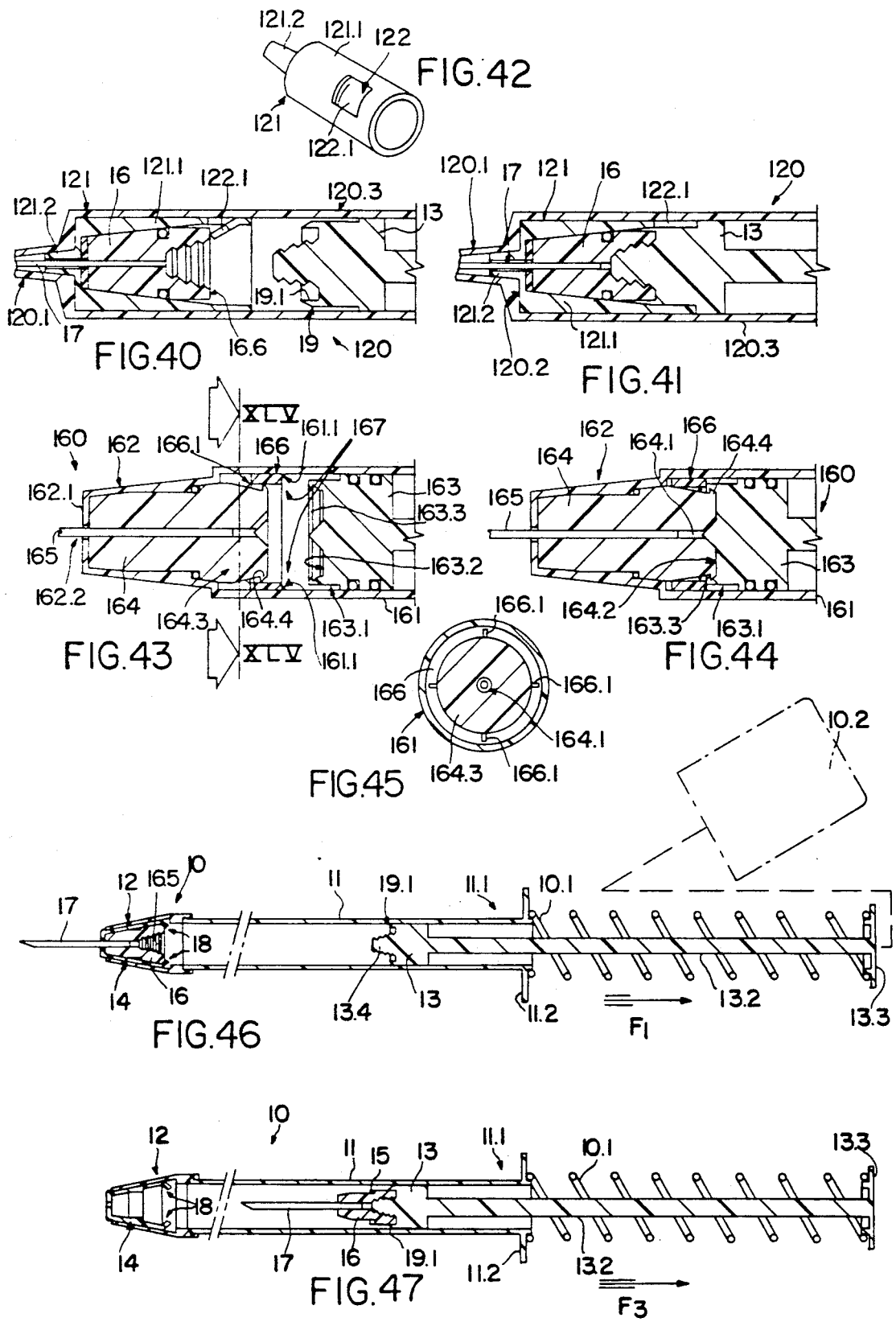

DISPOSABLE SAFETY SYRINGE

DESCRIPTION

The present invention relates to a disposable safety syringe, comprising a tubular syringe body with a needle-holder head integral with one of the tubular body's axial end zones, from which there extends an empty needle communicating, by means of a mounting bushing integral to the needle itself, with the cavity of the syringe body for injecting the liquids contained in the same cavity, and further comprising a plunger, housed in a tight and axially sliding fashion in the syringe body, and manually slide-driven by means of a shaft, with one of its axial end zones extending outside the syringe body through an aperture in this same body provided in its axial end zone opposite the needle-holder head.

Syringes of the specified type are generally used, for example, to inject liquid medications or to sample organic liquids, e.g. for purposes of therapy or medical analysis.

We are already familiar with disposable safety syringes which, at the end of the operation for injecting the liquid therein contained, enable one to manually cause the empty needle to withdraw inside the syringe body, or inside a tubular body for protecting this needle, and this is for safety purposes in disposing of the syringe in question. This operation is nonetheless dependent upon the willingness of the operator who, through forgetfulness, inexperience or on purpose, may leave the needle in a use position and hence in a dangerous position. This problem is especially serious today because of the numerous needle-bearing syringes discarded in public places, e.g. by drug addicts.

At the same time, prior disposable syringes may in practice be reused, with attendant risks of infection.

Furthermore, prior syringes of the specified type require direct intervention by the operator even during the stage for sucking the liquid up into the syringe body, necessitating the use of both of the operator's hands for a certain space of time, as well as a particular degree of manual steadiness.

It would also be desirable for the main components of syringes of the specified type to be thoroughly standardized and unified from the manufacturing standpoint.

It would further be desirable to use sterile test-tubes, e.g. laboratory test-tubes, which could if necessary be converted into injection syringe bodies and vice-versa, while it would prove remarkably convenient to be able to use phials containing injectable medications to serve as syringe bodies.

Accordingly, one purpose of the present invention is to provide a disposable safety syringe which, at the end of the operation for injecting the liquid therein contained, ensures that the empty needle automatically withdraws inside the syringe body, regardless of the operator's intentions, for safety purposes in disposing of the syringe itself. One further purpose is to provide a syringe as specified that cannot be subsequently used following its first use.

Yet another purpose is to provide a syringe as mentioned above, in which the liquid suction stage is carried out automatically, or at all events in an assisted manner by means of devices automatically governing the suction stroke of the syringe plunger.

An additional aim is to provide a syringe as indicated, in which at least some of the components can be standardized and unified, even in the case of syringes fulfilling different roles and serving different purposes.

Still another goal is to provide a syringe of the specified type, the body of which can if necessary serve as a laboratory test-tube, or phial for liquid medications and the like.

In view of these goals, the present invention provides a disposable safety syringe of the specified type, as characterized in claim 1 and in the following claims, as well as in the manner described hereunder.

BRIEF DESCRIPTION OF THE DRAWINGS

The invention shall now be described in detail with reference to the attached embodiment designs, in which:

FIG. 1 is an exploded view of a first embodiment of the disposable safety syringe according to the invention;

FIG. 2 is an axial cross-sectional view of the syringe according to claim showing how the syringe is presented for use; FIG. 3 is a view similar to FIG. 2, although showing the syringe at the conclusion of the stage for injecting a liquid contained therein;

FIGS. 4 and 5 are larger-scale detailed views of detail IV in FIG. 2 and detail V in FIG. 3 respectively;

FIG. 6 is a cross-sectional view according to line VI—VI in FIG. 2;

FIGS. 7 and 8 are views respectively similar to the views for FIGS. 4 and 5, although illustrating a second embodiment of the syringe according to the invention;

FIG. 9 is a cross-sectional view according to line IX—IX in FIG. 7;

FIGS. 10 and 11 are views respectively similar to the views for FIGS. 4 and 5, although illustrating a third way of carrying out the invention;

FIG. 12 is a larger-scale detailed view of detail XII in FIG. 11;

Figure 27:
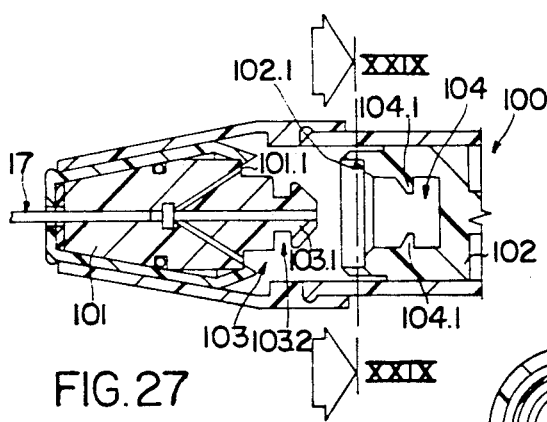
Figure 28:
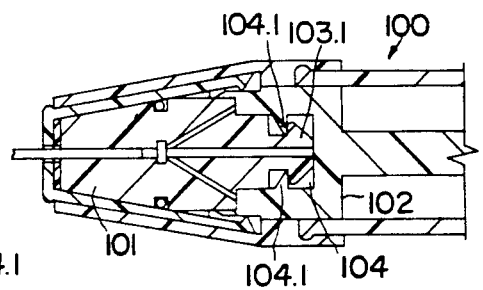
Figure 29:
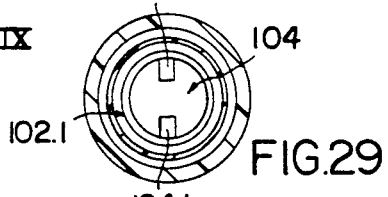
Figure 30:
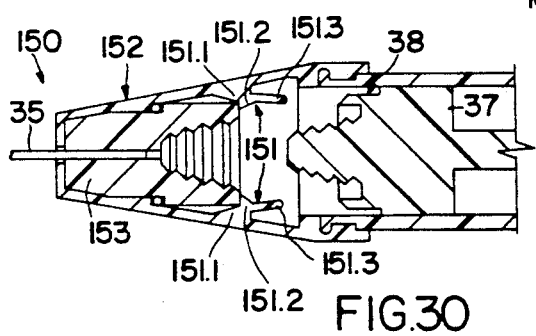
Figure 31:
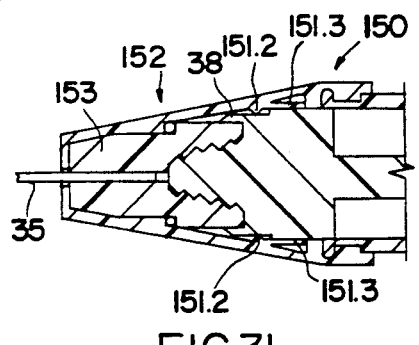

The thirteen pairs of figures respectively identified by the numbers: 13-14, 15-16, 17-18, 19-20, 21-22, 21-22, 23-24, 25-26, 27-28, 30-31, 32-33, 34-35, 40-41, and 43-44, illustrate, according to views respectively similar to those for FIGS. 4 and 5, the same number of additional embodiments of the syringe according to the invention;

FIG. 29 is a cross-sectional view according to line XXIX—XXIX in FIG. 27;

FIG. 35 is a cross-sectional view according to line XXXVI—XXXVI in FIG. 34;

FIGS. 37 and 42 illustrate, in perspective, respective embodiments of a capsule for housing a bushing for mounting the empty needle for the syringe according to the invention;

FIGS. 38 and 39 are axial-section views of a further embodiment of the syringe according to the invention, with the plunger respectively positioned in the starting position and in the end position for the stage for injecting the liquid contained in the syringe;

FIG. 45 is a cross-sectional view according to line XLV—XLV in FIG. 43;

FIGS. 46 and 47 are views similar to those for FIGS. 2 and 3, although showing the syringe according to those figures respectively at the end of the stage for sucking the injectable liquid, and upon completion of injection, in a position of safety with the needle retracted, ready for disposal.

FIRST EMBODIMENT OF THE INVENTION (FIGS. 1 TO 6)

With reference in the first instance to FIGS. 1 thru 6, the number 10 (FIGS. 1 to 3) marks the assembly of the disposable safety syringe according to the first embodiment of the invention.

Syringe 10 comprises a substantially cylindrical tubular syringe body 11, e.g. made of transparent plastic material, with a hollow needle-holder head 12 integral to one of its axial end zones. This needle-holder 12 is inserted onto syringe body 11, and consists of a cap, e.g. made of plastic material, having a cylindrical tubular body 12.1 coaxially pushed, tightly and by elastic release, over one free axial end zone of the cylindrical tubular body 11 of the syringe and prolonged into a coaxial, trunk-conical, integral hollow beak, 12.2, substantially like the neck of a syringe.

Syringe body 11 houses a tight and axially-sliding plunger 13, having a substantially cylindrical body, e.g. made of plastic material, bearing an annular elastic sealing gasket 13.1, e.g. made of rubber, fitted onto one of its circumferential grooves. This plunger 13 can be driven by axial sliding inside syringe body 11 between an axially advanced position up to inside needle-holder head 12, and an axially retracted position towards axial end zone 11.1 of syringe body 11 opposite the head 12—by means of an integral-body axial shaft 13.2. With its axial end zone distal from plunger 13, this shaft 13.2 extends outside syringe body 11, beyond axial end 11.1 of the plunger (FIGS. 2 and 3), and carries an integral discoidal actuating foot (13.3) integral to the shaft's end zone. A flange 11.2 is formed en bloc at axial end zone 11.1 of syringe body 11, providing the grip for the syringe 10. In partial reduction of this flange's (11.2) overall outline in a radial direction, are thereon formed two parallel rectilinear sides 11.3 (FIG. 6), the reasons which are discussed below.

In beak 12.2 of needle-holder head 12 there is engaged, coaxially and with slight forcing, a shell capsule 14 having an analogous trunk-conical shape, e.g. made of plastic material. At its smaller-diameter free axial end zone, this capsule 14 displays circumferential lip 14.1 delineating a frontal axial mouth 14.2. This lip 14.1 unfurls radially outwards from capsule 14 and emerges, with respect to the pertinent free axial end zone of the beak 12.2 of the needle-holder head 12, in such a way as to prevent capsule 14 from withdrawing in an axial direction from beak 12.2. Thereinside, trunk-conical capsule 14 displays an intermediate circumferential shoulder 14.3, formed by a wall zone 14.4 having a substantially cylindrical internal surface subdividing the conical cavity of capsule 14. An annular elastic sealing gasket 15, e.g. made of rubber, is juxtaposed against circumferential shoulder 14.3.

A bushing 16, for mounting coaxial empty syringe needle 17 is housed in capsule 14, coaxially and in retractable fashion, form-coupled for part of its axial extension, but not by forcing. Bushing 16 displays primary cylindrical section 16.1 with conically tapering free axial end zone 16.2, coupled in capsule 14, and wherein there is formed an axial through hole 16.3 for forced mounting of needle 17. Needle 17 extends axially from bushing 16 through frontal mouth 14.2 of capsule 14. The conically tapering end zone 16.2 of bushing 16 abuts directly in front of the circumferential lip 14.1 of capsule 14, thus preventing the forcing of bushing 16 inside the capsule. Bushing 16 further displays in a single body, and in a manner coaxial to primary cylindrical section 16.1, an additional cylindrical section 16.4 having a larger diameter, forming a circumferential step tightly juxtaposed against annular sealing gasket 15. This additional cylindrical section 16.4 of bushing 16 is received into capsule 14 with its free axial end zone radially overshooting and partly extending outside the capsule. In additional cylindrical section 16.4 of bushing 16, there is formed an axial coupling cavity 16.5, substantially conical and into which there emerges axial through hole 16.3. By means of its larger-diameter mouth, this axial cavity 16.5 communicates with the internal cavity of needle-holder head 12 and syringe body 11. Multiple undercut, coaxial, circumferential grooves are formed in axial cavity 16.5.

Empty needle 17 is securely maintained in the use position. i.e. axially extending from needle-holder head 12, by means of retaining means 18 (FIG. 1) integral with capsule 14 and acting upon bushing 16. These retaining means 18 consist of a pair of retaining arms 18.1, formed in a body integral with capsule 14 and therefrom extending beyond the capsule's larger-diameter axial end zone opposite frontal mouth 14.2, in a diametrically opposed position like a fork. These retaining arms 18.1 display their free end zone directed towards the axis of syringe 11 (FIG. 4), and are provided with pertinent retaining teeth 18.2. Retaining teeth 18.2 face one another. The retaining arms 18.1 between themselves receive the free axial end zone of the abovementioned additional cylindrical section 16.4 of bushing 16, and keep the bushing from withdrawing in an axial direction by means of their retaining teeth 18.2 engaged against the bushing's dorsal face 16.6, set against plunger 13 and whereupon there opens axial cavity 16.5. Retaining arms 18.1 and retaining teeth 18.2 do not interfere in the aperture of cavity 16.5.

Plunger 13 carries, in an integral body, an axial coupling head 13.4, substantially trunk-conical, extending from plunger's frontal face 13.5 turned towards bushing 16. This head 13.4 is arranged and shaped in such a way as to join the bushing's axial coupling cavity 16.5. Trunk-conical head 13.4 displays multiple annular projections capable of inseparably engaging the undercut grooves in cavity 16.5 of bushing 16. Axial coupling cavity 16.5 of bushing 16, and axial coupling head 13.4 of plunger 13, constitute the means of inseparable coupling between bushing 16 and plunger 13. This inseparable coupling is made substantially upon juxtaposition between dorsal face 16.6 of bushing 16 and frontal face 13.5 of plunger 13.

Means 19 for disengaging retaining means 18 (i.e. arms 18.1 with retaining teeth 18.2) from bushing 16 for mounting needle 17, are further provided integral to plunger 13. These disengagement means 19 comprise a rigid annular collar 19.1 extending from frontal face 13.5 of plunger 13, in a body integral and coaxial to plunger 13 and hence to axial coupling head 13.4, from which it is radially distanced. This collar 19.1 is designed to strike, externally and for part of its axial length, the free axial end zone of the larger-diameter, additional cylindrical section 16.4 of bushing 16. The free circumferential edge of collar 19.1 is beveled to enable easy engagement by gradual axial forcing of the collar between and against retaining teeth 18.2 integral with retaining arms 18.1, in the manner of a mechanism for spreading these arms towards the wall of beak 12.2 of needle-holder head 12. Full spreading is achieved in step with the axial penetration and inseparable coupling of the plunger's coupling head 13.4 with the bushing's coupling cavity 16.5 (FIG. 5). In such a state, bushing 16 may be axially retracted from capsule 14.

The external diameter of annular collar 19.1, in addition to the diameter of the anterior portion of plunger 13 proximal to the collar, are smaller than the diameter of the remaining portion of plunger body 13. In this way, when collar 19.1 is pushed onto additional cylindrical section 16.4 of bushing 16, a free annular space (18.3) is formed (FIG. 5) between collar 19.1, the anterior portion of plunger 13, and needle-holder head 12 sufficient to accommodate the arms 18.1 with retaining teeth 18.2, kept elastically spread by collar 19.1.

The syringe 10 further comprises means for automatically returning plunger 13 to a retracted position towards axial end 11.1 of syringe body 11, upon completion of the stage for injecting the liquid contained in the syringe body. These means of automatic return comprise a helicoidal compression spring 10.1 interposed, in a manner coaxial to shaft 13.2 of plunger 13, between the shaft's discoidal actuating foot 13.3 and the flange 11.2 of syringe body 11. Centering crowns 13.30 and 11.20 (FIG. 3) for return spring 10.1 are formed integral and coaxial on the opposing faces of discoidal foot 13.3 and flange 11.2.

A rigid cap 10.2 for safety and protection, consisting of a cylindrical cup, e.g. made of plastic material, is coaxially fitted onto that portion of shaft 13.2 extending beyond syringe body 11, with its base wall resting against the shaft's discoidal foot 13.3. With its mouth zone, this cap 10.2 strikes the flange 11.2 of syringe body 11. On the internal wall of its cylindrical wall and at its mouth, this cap 10.2 displays two diametrically opposite pairs of tongues 10.3, shaped like circular segments capable of assuming a position of noninterference at the rectilinear sides 11.3 of flange 11.2 of syringe body 11. Accordingly, with cap 10.2 rotated substantially by ninety degrees (FIG. 6) with respect to the abovementioned noninterference position, and with flange 11.2 of syringe body 11 arranged between these pairs of tongues 10.3, the cap 10.2 proves to be securely anchored to syringe body 11, even through the elastic axial thrust action exerted by spring 10.1. The height of cap 10.2 is such that, once anchored, said cap keeps plunger 13 in an axially advanced position in the syringe body 11 up to being in proximity with bushing 16, but without contact therewith (FIGS. 2 and 4), thereby causing preloading in return spring 10.1. This position of plunger 13 is firmly and securely maintained until cap 10.2 is manually disengaged from flange 11.2 of syringe body 11.

SECOND EMBODIMENT OF THE INVENTION
(FIGS. 7-9)

20 marks the syringe in its entirety according to this second embodiment of the invention. This comprises a cylindrical tubular syringe body 21 with empty needle-holder 22, integral to one of its axial end zones. Needle-holder 22 is inserted onto syringe body 21, and consists of a cap having a cylindrical body 22.1 tightly pushed and engaged by screwing, by means of an internally threaded axial extremity, onto a likewise externally threaded axial end zone of syringe body 21. Cylindrical tubular body 22.1 is prolonged into a coaxial, trunk-conical, integral hollow beak 22.2, substantially like the neck of a syringe. On its free axial end zone, this hollow beak 22.2 displays a circumferential lip 22.3 delineating a frontal axial mouth 22.4. Into this hollow beak 22.2 there is inserted an annular elastic sealing gasket 23, resting against the beak's circumferential lip 22.3 and having its hole coaxial to frontal mouth 22.4.

In addition, the beak 22.2 of needle-holder 22 houses, coaxially and form-coupled for part of its axial length, but not by forcing, a retractable bushing 24 for mounting a coaxial, hollow syringe needle 25. Bushing 24 displays primary trunk-conical section 24.1, coupled into hollow beak 22.2, and wherein there is formed an axial through hole 24.2 for forced mounting of needle 25. Needle 25 extends axially from the bushing through frontal mouth 22.4 of needle-holder head 22. Trunk-conical section 24.1 of bushing 24 abuts against annular sealing gasket 23, thus preventing the forcing of the bushing inside beak 22.2. Furthermore, in one of its circumferential grooves, trunk-conical section 24.1 carries an additional annular elastic sealing gasket 23.1. Bushing 24 further displays, in a single body with the primary trunk-conical section 24.1., a secondary, coaxial cylindrical section 24.3, extending with its free axial end zone up till the space in cylindrical tubular body 22.1 of needle-holder head 22, out of contact with respect to the wall of the tubular body. In cylindrical section 24.3 of bushing 24, there is formed a substantially conical, axial coupling cavity 24.4 into which there emerges the axial through hole 24.2. By means of its larger-diameter mouth, axial cavity 24.4 communicates with the internal cavity of needle-holder head 22 and thus of syringe body 21. Multiple undercut, coaxial, circumferential grooves are formed in axial coupling cavity 24.4.

Empty needle 25 is securely maintained in the use position, i.e. axially extending from needle-holder head 22, by means of retaining means 26 (FIG. 9), integral to needle-holder head 22 and acting upon bushing 24. These retaining means 26 consist of a retaining ring 26.1, e.g. made of plastic material, securely housed by elastic release in a circumferential groove (not given a reference number in the drawings) provided on the inner face of cylindrical tubular body 22.1 of needle-holder head 22, in a position directly upstream from bushing 24, according to the direction of injection of liquids into syringe 20. The internal diameter of retaining ring 26.1 is significantly greater than the maximum cross-sectional outline dimension of bushing 24 (diameter of the cylindrical section 24.3 of bushing 24). For assembly purposes, the retaining ring 26.1 is substantially "C"-shaped (FIG. 9). In an integral body, retaining ring 26.1 carries a pair of retaining teeth 26.2, diametrically opposed and bent towards the bushing 24. With their free end zone, these retaining teeth engage dorsal face 24.5 (FIG. 9) of bushing 24. These retaining means 26 accordingly prevent the bushing—and hence needle 25—from withdrawing in an axial direction.

Tubular syringe body 21 houses, in a tight and axially-sliding fashion, a plunger 27 wholly similar to plunger 13 illustrated and described with reference to FIGS. 1 to 6. In common with plunger 13, plunger 27 displays a trunk-conical, integral, axial coupling head, here marked 27.1, extending from its frontal face 27.2 turned towards the bushing 24. Coupling head 27.1 is arranged and shaped to inseparably join axial coupling cavity 24.4 of bushing 24, and constitutes, with that cavity, the means of inseparable coupling between bushing 24 and plunger 27. This inseparable coupling is achieved upon juxtaposition between dorsal face 24.5 of bushing 24 and frontal face 27.2 of plunger 27 (FIG. 8).

Plunger 27 further carries integral means 28 for disengaging retaining means 26 from bushing 24. These disengagement means 28 consist of a rigid annular collar 28.1, extending from the frontal face 27.2 of plunger 27, integral and coaxial to said plunger and hence to its trunk-conical head 27.1, from which it is radially distanced in a manner entirely similar to annular ring 19.1 of plunger 13. This collar 28.1 is designed to strike, externally and for part of its axial length, the free axial end zone of cylindrical section 24.3 of bushing 24. The external diameter of annular ring 28.1 is smaller than the internal diameter of retaining ring 26.1, in such a way as to be received there, passing through without interferences. The free circumferential edge of annular collar 28.1 is beveled to enable easy engagement by gradual axial forcing of said collar between and against retaining teeth 26.2 integral with said retaining ring, in the manner of a mechanism for spreading these teeth towards the wall of cylindrical tubular body 22.1 of needle-holder head 22. Full spreading is achieved in step with the axial penetration and inseparable coupling of the plunger's coupling head 27.1 with axial coupling cavity 24.4 of bushing 24. In such a state, bushing 24 may be axially retracted from needle-holder head 22, by axially passing through retaining ring 26.1. Furthermore, the external diameter of annular collar 28.1 and the diameter of the anterior portion of plunger 27 proximal to said collar are of equal dimension, less than the dimension of the diameter of the remaining portion of plunger 27. In this way, when collar 28.1 is pushed onto cylindrical section 24.3 of bushing 24, a free annular space (28.2) is formed (FIG. 8) between this collar, the anterior portion of the plunger, and the needle-holder head, sufficient to accommodate retaining teeth 26.2, kept elastically spread by collar 28.1.

Otherwise, syringe 20 is no different from syringe 10 according to FIGS. 1 to 6, and for this reason we shall dispense with any further description.

THIRD EMBODIMENT OF THE INVENTION (FIGS. 10-12)

30 marks the syringe in its entirety according to the third way of carrying out the invention. This comprises a cylindrical tubular syringe body 31 having a hollow needle-holder head 32, integral at one of its axial end zones. Needle-holder head 32 is inserted onto syringe body 31, and consists of a cap, e.g. made of plastic material, having a cylindrical tubular body 32.1 coaxially pushed, tightly and by elastic release, onto an axial end zone of syringe body 31. Tubular body 32.1 of needle-holder head 32 is prolonged into a coaxial, trunk-conical, integral hollow beak 32.2, substantially like the neck of a syringe. At its free axial end zone, hollow beak 32.2 displays a circumferential lip delineating a frontal axial mouth 32.4. Into these hollow cavity 32.2 there is inserted an annular elastic sealing gasket 33, resting against the beak's circumferential lip 32.3, and having its hole coaxial with frontal mouth 32.4.

Trunk-conical beak 32.2 of needle-holder head 32 also houses, coaxially and form-coupled for part of its axial extension, but not by forcing, a retractable bushing 34 for mounting a coaxial, hollow syringe needle 35. Bushing 34 displays primary trunk-conical section 34.1 coupled into hollow beak 32.2, and wherein there is formed an axial through hole 34.2 for forced mounting of needle 35. Needle 35 axially extends from the bushing through frontal mouth 32.4 of needle-holder head 32. Trunk-conical section 34.1 abuts against annular sealing gasket 33, thus preventing the forcing of the bushing inside beak 32.2. Furthermore, in one of its circumferential grooves, trunk-conical section 34.1 carries an additional annular elastic sealing gasket 33.1. In a single body with primary trunk-conical section 34.1, bushing 34 further displays a secondary coaxial, cylindrical section 34.3, extending with its free, reduced-diameter axial end zone, 34.4, into the space in needle-holder head 32, out of contact with respect to the wall of said needle-holder head. A circumferential shoulder 34.5 (FIG. 12) is provided between cylindrical section 34.3 of bushing 34 and its free axial end zone 34.4. In cylindrical section 34.3, having free axial end zone 34.4, of bushing 34 there is formed an axial coupling cavity 34.6, substantially conical and into which there emerges the axial through hole 34.2. By means of its larger-diameter mouth, this axial cavity 34.6 communicates with the internal cavity of needle-holder head 32 and hence with syringe body 31. Multiple undercut, coaxial, circumferential grooves are formed in axial cavity 34.6.

Empty needle 35 is securely fastened in the use position, i.e. axially extending from needle-holder head 32, by means of retaining means 36, integral to needle-holder head 32 and acting upon the bushing 34. These retaining means 36 consist of a pair of retaining teeth protruding into the space of needle-holder head 32 from the inner face of trunk-conical beak 32.2. These retaining teeth 36.1 are formed in a body integral with needle-holder head 32, in proximity with its cylindrical tubular body 32.1, and are diametrically opposed and oriented substantially towards needle 35. With their free end zone, these retaining teeth 36.1 engage circumferential shoulder 34.5 of bushing 34. In this way, retaining means 36 keep the bushing, and hence needle 35, from withdrawing in an axial direction.

Tubular syringe body 31 houses, in a tight and axially-sliding fashion, a plunger 37 wholly similar to plunger 13 illustrated and described with reference to FIGS. 1 thru 6. In common with plunger 13, plunger 37 displays a trunk-conical, integral, axial coupling head, here shown with 37.1, and extending from its frontal face 37.2 turned towards bushing 34. Coupling head 37.1 is arranged and shaped to inseparably join axial cavity 34.6 of bushing 34, and constitutes, with that selfsame cavity, the means of inseparable coupling between bushing 34 and plunger 37. This inseparable coupling is achieved upon juxtaposition between dorsal face 34.7 of bushing 34 and frontal face 37.2 of plunger 37 (FIG. 11).

Plunger 37 further carries integral means 38 for disengaging retaining means 36 from bushing 34. These disengagement means 38 consist of a rigid annular collar 38.1, extending from frontal face 37.2 of plunger 37, integral and coaxial to the plunger itself and hence to its trunk-conical head 37.1, from which said annular collar is radially distanced in a manner wholly similar to annular collar 19.1 of plunger 13. This collar 38.1 is designed to externally strike the free axial end zone 34.4 of bushing 34. The free circumferential edge of annular collar 38.1 is beveled to enable easy engagement by progressive axial forcing of this collar between and against retaining teeth 36.1, integral with needle-holder head 32, in the manner of a mechanism for spreading these teeth towards the wall of the needle-holder head. Full spreading is achieved in step with the axial penetration and inseparable coupling of the plunger's coupling head 37.1 with coupling cavity 34.6 of bushing 34. In such a state, bushing 34 may be axially retracted from needle-holder head 32.

In addition, the external diameter of annular collar 38.1 and the diameter of the anterior portion of plunger 37 proximal to said collar, are of a smaller dimension than the dimension for the diameter of the remaining portion of plunger 37. In this way, when collar 38.1 is pushed onto the free axial end zone 34.4 of bushing 34, a free annular space (38.2) is formed between this collar, the anterior portion of the plunger, and the needle-holder head, sufficient to accommodate the retaining teeth 36.1, kept elastically spread by collar 38.1.

Otherwise, syringe 30 is no different from syringe 10 according to FIGS. 1 thru 6, and for this reason we shall dispense with any further description.

With comparative reference to the first embodiment of the invention, we shall now explain additional embodiments (fourth thru twelfth) of the syringe according to the invention.

In the figures in the attached drawings illustrating the abovementioned embodiments of the invention, the parts substantially similar to the parts in the syringe depicted in FIGS. 1 thru 6 shall be indicated with the same reference numbers.

For parts not explicitly mentioned, please refer to the explanation given for the first embodiment of the invention.

In all of the following embodiments, from the fourth to the twelfth, a bushing for mounting the empty syringe needle shall be housed, in an axially retractable manner, in a capsule, which shall in its turn be inserted and securely bound into the syringe's needle-holder head. Means for retaining this needle in the use position, integral to this capsule, act upon said bushing, in a manner disengageable therefrom, to prevent the bushing from withdrawing in an axial direction.

FOURTH EMBODIMENT OF THE INVENTION (FIGS. 13-14)

The syringe according to the invention is here marked 40 in its entirety. This syringe 40 differs from syringe 10 (FIGS. 1-6) essentially in regard to the means for retaining empty syringe needle 17 in the use position.

These retaining means, here marked 41 in their entirety, comprise a pair of retaining arms 41.1 integral to a capsule 42, forced into the hollow beak 12.2 of syringe 40 and wholly similar to capsule 14 for syringe 10. These retaining arms 41.1 also have a structure similar to the structure for arms 18.1 in syringe 10, albeit prolonged, in comparison with arms 18.1, beyond the pertinent retaining tooth, here shown with 41.2, which these arms also carry. These retaining arms 41.1 converge between themselves and keep bushing 16 from withdrawing in an axial direction by means of their retaining teeth 41.2 engaged against the dorsal face of said bushing. In addition, they form a fork that can be engaged and elastically spread by disengagement means 19 integral with plunger 13, in a more gradual and amenable fashion. This makes it easier to disengage retaining teeth 41.2 from bushing 16.

FIFTH EMBODIMENT OF THE INVENTION (FIGS. 17-18)

The syringe according to the invention is here marked 50 in its entirety. Syringe 50 differs from syringe 10 (FIGS. 1-6) essentially in regard to the means of inseparable coupling between the bushing for mounting the empty needle, here shown with 51, and the plunger, marked 52. Plunger 52 displays a conical axial coupling cavity 52.1, open with its mouth at the plunger's frontal face 52.2. Multiple undercut, coaxial, circumferential grooves are formed in said axial cavity 52.1.

Bushing 51 displays an integral, trunk-conical, axial coupling head 51.1, extending from the bushing's dorsal face 51.2 turned towards plunger 52.

Axial coupling head 51.1 and axial coupling cavity 52.1 are arranged and shaped in such a way as to join inseparably upon juxtaposition between frontal face 52.2 of plunger 52 and dorsal face 51.2 of bushing 51. It will be noted that in bushing 51, the axial through hole, marked 51.3, for mounting empty needle 17, proceeds along the entire axial length of the bushing and of the coupling head, and that from this hole there branch out additional liquid channels 51.4, emerging at the base of the axial coupling head 51.1.

SIXTH EMBODIMENT OF THE INVENTION (FIGS. 19-20)

The syringe according to the invention is here marked 60 in its entirety. This differs from syringe 10 (FIGS. 1-6) essentially in regard to the means for retaining empty syringe needle 17 in the use position, as well as in regard to the means for disengaging these retaining means from the bushing for mounting the needle, here marked 61.

Bushing 61 is housed, in an axially retractable manner, in a capsule 62, substantially similar to capsule 14 for syringe 10, and it extends outside said capsule with its axial end zone distal from hole 17. An integral annular projection 61.1 is formed at said axial extremity zone.

In an integral body, capsule 62 carries the retaining means marked 63 in their entirety. These consist of a pair of retaining arms marked 63.1, extending from the large-diameter, free circumferential edge of capsule 62 and turned in a direction converging towards the plunger for syringe 60, indicated with 64. These retaining arms 63.1 are diametrically opposed and form an elastically spreadable fork. On each of these retaining arms is provided a retaining notch 63.2, in which is engaged the abovementioned annular projection 61.1 of bushing 61. In this way, these retaining arms 63.1 keep the bushing, and hence needle 17, from withdrawing in an axial direction.

65 marks the means for disengaging these retaining means 63 from bushing 61. These consist of a spreader collar 65.1 formed in a body integral with plunger 64, at the base of an axial coupling head 64.1 extending en bloc from the plunger's frontal face opposite bushing 61. This spreader collar 65.1 conically tapers in the direction of bushing 61, and it is provided in order to be engaged between and against the retaining arms 63.1, forming a fork. This causes the retaining arms 63.1 to spread elastically towards the wall of needle-holder head 12, as a consequence of its progressive axial forcing between these retaining arms. Full spreading is achieved upon juxtaposition of spreader collar 65.1 against bushing 61. In such a state, annular projection 61.1 of bushing 61 may be disengaged from the retaining notches 63.2 of arms 63.1, as these notches are now opened towards plunger 64. In this way, bushing 61 may be axially retracted from capsule 62.

The needle-holder head is provided with an annular space 65.2, for accommodating the elastically spread retaining arms 63.1.

SEVENTH EMBODIMENT OF THE INVENTION (FIGS. 23-24)

The syringe according to the invention is here marked 70 in its entirety. Syringe 70 is substantially similar to syringe 50 according to FIGS. 17 and 18. It essentially differs in that it comprises a empty needle-holder head 71 fitted coaxially, tightly and by elastic release, onto a cylindrical tubular syringe body 72.

Tubular body 72 houses a tight and axially-sliding plunger 73. In a position proximal to its shaft 73.1, plunger 73 displays an integral annular collar 73.2 projecting from its cylindrical body 73.3 and making a seal with syringe body 72. The cylindrical body 73.3 of the plunger may penetrate proportionately into needle-holder head 71.

EIGHT EMBODIMENT OF THE INVENTION (FIGS. 34-37)

The syringe according to the invention is here marked 80 in its entirety. It differs from syringe 10 (FIGS. 1-6) essentially in regard to the means for retaining needle 17 in the use position, the which means are provided integral to a capsule 81 for accommodating, in an axially retractable manner, the bushing 16 for mounting the needle. Capsule 81, e.g. made of plastic material, is forced into the hollow beak 12.2 of syringe 80.

Capsule 81 displays a trunk-conical shell 81.1, prolonging itself into a substantially cylindrical section of integral shell 81.2. In this cylindrical shell section 81.2 are provided two integral retaining tongues 82.1, curved, notched and folded with respect to shell section 81.2. in such a way as to display their free end zone extending towards the interior of capsule 81. These retaining tongues 82.1 integral to capsule 81, constitute the means for retaining needle 17 in the use position, and are marked 82 in their entirety in FIG. 37. These retaining tongues 82.1 do in fact abut with their free end zones against dorsal wall 16.6 of bushing 16 for mounting needle 17, thus preventing the bushing from withdrawing in an axial direction.

The means for disengaging these retaining means 82 are substantially identical to those for syringe 10, and are here marked 19. Their annular collar 19.1 integral to plunger 13 is provided in order to be axially forced progressively to engage the retaining tongues 82.1—by penetrating into capsule 81 in the manner of a spreader mechanism—ultimately pushing them back, through elastic bending, onto the peripheral cylindrical outline of shell section 81.2 of capsule 81 (FIG. 35). This annular collar 19.1 is further provided in order then to strike the free axial end zone of bushing 16 which extends inside this cylindrical shell section 81.2, out of contact with the shell. In such a state, bushing 16 may be axially retracted from capsule 81.

NINTH EMBODIMENT OF THE INVENTION (FIGS. 25-26)

The syringe according to the invention is here marked 90 in its entirety. It differs from syringe 80, described above with reference to FIGS. 34 to 37, essentially in that it displays a cylindrical tubular syringe body 91, carrying a syringe neck or head 92. This syringe body 91 with integral neck 92 is of the conventional type, and is commercially available. It lends itself to the insertion by slight forcing into syringe body 91, of a capsule 93, housing a bushing for mounting a empty needle 17.

Capsule 93 displays a cylindrical shell 93.1 delineating a trunk-conical axial cavity for housing bushing 16. At one of its axial ends, this cylindrical shell 93.1 carries an integral tube 93.2, coaxial, having a trunk-conical profile, communicating with the axial cavity of capsule 93. This tube 93.2, through which empty needle 17 extends, is engaged into syringe head 92, tightly and by forcing, whereas shell 93.1 abuts against the bottom wall 91.1 of syringe body 91. At its other axial end, this shell 93.1 displays integral tongues 93.3 for retaining the bushing 16 against axial withdrawal. These retaining tongues 93.3 are wholly similar to the retaining tongues 82.1 for capsule 81 (FIGS. 34 to 37), and for that reason we shall dispense with any further description.

TENTH EMBODIMENT OF THE INVENTION (FIGS. 27-29)

The syringe according to the invention is here marked 100 in its entirety. It is substantially similar to syringe 50 according to FIGS. 17 and 18. It differs only in relation to the conformation of the means for inseparable coupling between the bushing for mounting empty syringe needle 17—the bushing is here marked 101—and the plunger for the syringe, shown with 102.

In an integral body, bushing 101 carries an axial coupling head 103, extending from its dorsal face 101.1 turned towards plunger 102. Axial coupling head 103 displays a trunk-conical nib 103.1 extending from a coaxial cylindrical stem 103.2 having a smaller diameter. The nib 103.1 conically tapers towards plunger 102.

By the same token on frontal face 102.1 of plunger 102 set against bushing 101, there is formed a substantially cylindrical axial coupling cavity 104, capable of receiving coupling head 103, and from whose side wall two diametrically opposed lock teeth 104.1 project in a radial direction. These lock teeth 104.1 are reciprocally interdistanced to a degree corresponding to that of the diameter of stem 103.2 of coupling head 103. Lock teeth 104.1 display their respective faces turned towards the bushing 101, trending towards the bottom of coupling cavity 104. Through their elastic deformation, these lock teeth enable nib 103.1 to axially penetrate into coupling cavity 104 up to and beyond the teeth themselves, albeit preventing this nib from being extracted from coupling cavity 104 once the nib has overshot the teeth 104.1.

ELEVENTH EMBODIMENT OF THE INVENTION (FIGS. 38-39)

The syringe according to the invention is here marked 110 in its entirety. This differs from syringe 10 (FIGS. 1-6) essentially in regard to its syringe body and the plunger, here marked 111 and 112 respectively.

Syringe body 111 is substantially cylindrical and tubular, and at one of its axial ends it carries an integral standardized attachment 111.1, cylindrical and tubular, coaxial, and threaded on its outside. Tightly engaged by screwing onto this standardized attachment 111.1, is a needle-holder head 113 having a cylindrical tubular body 113.1 internally threaded in like manner. Into this needle-holder head 113 there is inserted, by axial forcing, a capsule 14 with needle-holder bushing 16 and empty needle 17 substantially similar to their counterparts in syringe 10.

According to the illustrated example, syringe body 11 displays a diameter appreciably greater than the diameter for standardized attachment 111.1, and at its other axial end it carries a separable base 114, engaged there by means of a bayonet joint (radial lock projections 111.2 on syringe body 111 and substantially "L"-shaped through notches lying on the base 114). This base 114 displays an axial hole 114.2, passing through which there is arranged and slide-driven a plunger shaft 115, that can be disengaged from plunger 112 and displaying one of its axial ends free and threaded, inserted into syringe body 111.

Plunger 112, inserted in a tight and axially-sliding fashion into syringe body 111, displays, on its dorsal face 112.1 turned towards shaft 115, a matchingly threaded axial cavity 112.2 onto which the free, threaded end of shaft 115 may be engaged by screwing.

Between base 114 and discoidal actuating foot 115.1 of shaft 115 there is interposed, in a manner coaxial to said shaft, a helicoidal compression spring 116, according to an arrangement similar to the arrangement for spring 10.1 in syringe 10.

Plunger 112 further displays an integral, cylindrical, axial headpiece 112.3, having a diameter substantially matching the internal diameter of standardized attachment 111.1, and extending from its frontal face 112.4 turned towards needle-holder head 113. Headpiece 112.3 is received through axial sliding into standardized attachment 111.1 on syringe body 111, in such a way as to ensure that substantially all the liquid contained in syringe 110 is discharged through this same attachment.

Headpiece 112.3 frontally carries en bloc an axial coupling head 13.4 and an annular collar 19.1 wholly similar to their counterparts in syringe 10.

TWELFTH EMBODIMENT OF THE INVENTION (FIGS. 40-42)

Figure 23:
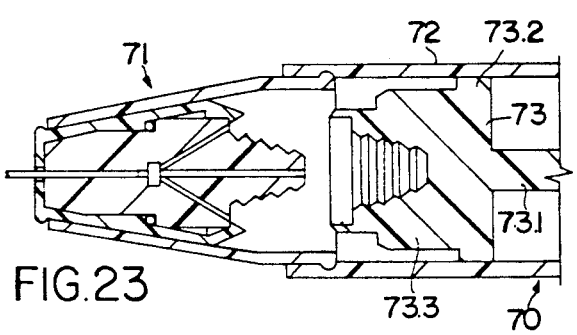
Figure 24:
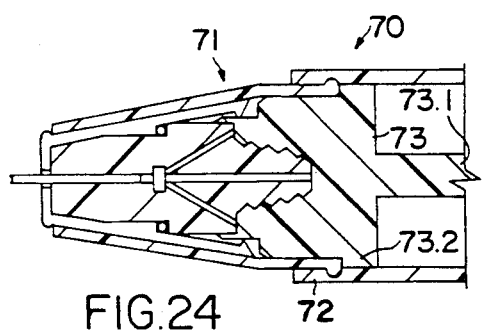
Figure 25:
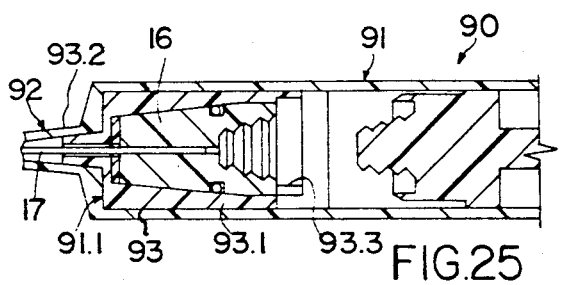
Figure 26:
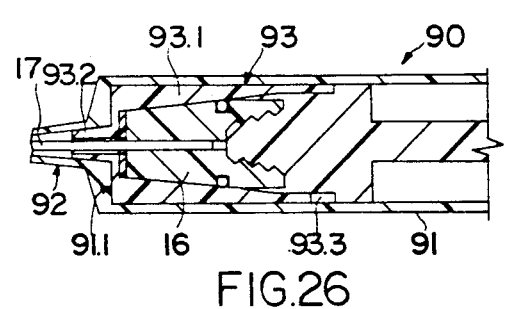

The syringe according to the invention is here marked 120 in its entirety. This substantially corresponds to syringe 90 according to FIGS. 25 and 26. It differs essentially in regard to the means for retaining needle 17 in the use position, the which means, integral to a capsule, are here indicated with 121.

In common with capsule 93 (FIGS. 25-26), this capsule 121, which houses the bushing 16 in an axially retractable manner, displays a cylindrical shell 121.1, delineating a trunk-conical cavity for housing the bushing 16 for mounting empty needle 17. At one of its axial end zones, the shell 121.1 carries an integral, coaxial tube, having a trunk-conical profile, 121.2. The tube, through which empty needle 17 extends, is tightly engaged by slight forcing into syringe neck or head 120.1 of syringe 120, while the shell 121 abuts against the bottom wall 120.2 of tubular syringe body 120.3 of the syringe. In the shell of capsule 121 there is formed an integral retaining tongue 122.1, notched and bent away from this same shell towards the interior of capsule 121. This tongue 122.1 integral to capsule 121, constitutes the means for retaining the needle 17 in the use position, the which means are marked 122 in their entirety in FIG. 42. The retaining tongue 122.1 is in fact engaged with its free end zone against the dorsal wall 16.6 of bushing 16, thus preventing the bushing from withdrawing in an axial direction.

The means for disengaging these retaining means 122 from bushing 16 are substantially similar to those for syringe 10 and are here also marked 10. Their annular collar 19.1, integral to plunger 13, is provided in order to be axially forced—by penetrating into capsule 121 in the manner of a spreader mechanism—to gradually engage this retaining tongue 122.1, until ultimately pushing it back, through elastic bending, onto the peripheral outline of capsule 112.

Collar 19.1 is further provided in order then to partially strike the free axial end zone of bushing 16 proximal to plunger 13, which extends into this shell out of contact with respect to the shell itself. In such a state, bushing 16 may be axially retracted from capsule 122.

With reference to the third embodiment of the invention (FIGS. 10-12), we shall now explain three further ways of carrying out the invention (thirteenth to fifteenth). Parts substantially similar to the parts of syringe 10 according to FIGS. 10-12 are shown with the same reference numbers and are not explained any further. For parts not explicitly mentioned, please refer to the explanation given for the third embodiment of the invention, as well as for the first embodiment of the invention (FIGS. 1-6).

In all the following embodiments of the invention, from the thirteenth embodiment to the fifteenth embodiment, a bushing for mounting the hollow syringe needle is tightly housed directly in the needle-holder head of the syringe itself, with the possibility of retraction in an axial direction. The means for retaining this needle in the use position, the which means are integral with the needle-holder head, act upon the bushing, in a manner disengageable therefrom, to prevent the bushing from withdrawing in an axial direction.

THIRTEENTH EMBODIMENT OF THE INVENTION (FIGS. 15-16)

The syringe according to the invention is here marked 130 in its entirety. It differs from syringe 30 (FIGS. 10-12) essentially in regard to the conformation of the needle-holder head, here marked 131, and in regard to the bushing for mounting the empty needle, here marked 132, tightly inserted into the same needle-holder head. 35 marks the empty needle.

Needle-holder head 131 is inserted onto the tubular syringe body 31 and displays a cylindrical tubular body 131.1 coaxially inserted, tightly and by elastic release, onto tubular syringe body 31. This body 131.1 of the needle-holder head displays en bloc a hollow syringe neck 131.2, out of axial alignment with the body 131.1.

By the same token, needle-holder bushing 132 displays a substantially trunk-conical primary section 132.1 coupled tightly, but not by forcing, into syringe neck 131.2. This substantially trunk-conical primary section 132.1 is prolonged into an integral, substantially cylindrical secondary section 132.2, extending with its smaller-diameter, free axial end zone 132.3 into the space for the cylindrical tubular body 131.1 of needle-holder head 131, out of contact with the wall of that body. In bushing 132, the primary section 132.1 and secondary section 132.2 are out of axial alignment with one another, with secondary section 132.2 and the corresponding free axial end zone 132.3 being coaxial with syringe body 31.

FOURTEENTH EMBODIMENT OF THE INVENTION (FIGS. 21-22)

The syringe according to the invention is here marked 140 in its entirety. Syringe 140 displays cylindrical tubular body 141, e.g. made of plastic material, having a trunk-conical, integral needle-holder head 142, like the neck of a syringe. Into this needle-holder head 142, there is tightly inserted a bushing for mounting empty needle 35, here marked 143. With its substantially cylindrical free axial end zone 143.1, bushing 143 extends into the space for the needle-holder head 142, coaxially and out of contact with the wall thereof. Bushing 143 is kept from withdrawing in an axial direction by retaining means marked 144 in their entirety. These comprise a pair of retaining teeth 144.1, formed en bloc with needle-holder head 142 and projecting into the space thereof, substantially in the direction of needle 35. These retaining teeth 144.1 are diametrically opposed, and with their free end zone they engage the dorsal wall 143.2 of bushing 143. At these retaining teeth 144.1, the wall of the needle-holder head 142 is made noticeably thinner by means of external circumferential groove 141.1.

Plunger 145 is received into syringe body 141 in a tight and axially-sliding fashion. Plunger 145 displays its anterior axial end zone 145.1, proximal to bushing 143, with a reduced diameter in such a way as to penetrate into a cylindrical spreader ring 146, provided for the purpose of disengaging retaining teeth 144.1 from bushing 143. This spreader ring 146 is interposed in the syringe body 141, between bushing 143 and plunger 145, upstream from teeth 144.1, in the direction of injection of the liquid in this syringe, and can be partially fitted onto the free axial end zone 143.1 of bushing 143, and is arranged to freely slide in contact with the wall of this syringe body up onto the needle-holder head 142. The height of spreader ring 146 is greater than the axial extension of the anterior axial end zone 145.1 of plunger 145, in such a way that, once pushed onto the plunger's axial end zone and on a ledge against plunger body 145, the ring 146 extends partially from the plunger towards the bushing 143. This ring 146 may thus be pushed onto axial end zone 145.1 of plunger 145 and partially fitted onto free axial end zone 143.1 of bushing 143, as a result of the advancement of plunger 145 in an axial direction. Furthermore, the circumferential edge of ring 146 that faces bushing 143 is beveled to enable easy engagement by gradually axial forcing thereof between and against retaining teeth 144.1 integral with needle-holder head 142, in the manner of a mechanism for spreading these teeth towards the wall of the needle-holder head. This operation is facilitated by the elastic pliability of needle-holder head 142 at its circumferential groove 141.1 (FIG. 22).

FIFTEENTH EMBODIMENT OF THE INVENTION (FIGS. 30-31)

The syringe according to the invention is here marked 150 in its entirety. Syringe 150 differs from syringe 30 (FIGS. 10-12) essentially in regard to the means for retaining empty needle 35 in the use position. These retaining means are here marked 151 in their entirety, and consist of a pair of retaining arms 151.1 integral to the wall of the needle-holder head, marked 152, of the syringe. The retaining arms 151.1 are extended into the space for the same needle-holder head, and in the proximity of their base, they display a retaining tooth 151.2, engaged against the dorsal face of bushing 153 for mounting empty needle 35, tightly inserted into needle-holder head 152. In this way, the bushing is prevented from withdrawing in an axial direction. These retaining arms 151.1 are prolonged beyond tooth 151.2 by pertinent arm sections 151.3 extending in a direction converging towards plunger 37, which is arranged to tightly slide in syringe body 31, thus forming an elastically spreadable fork by means of the retaining means 38 integral to plunger 37. This makes it easier to disengage retaining teeth 151.2 from bushing 153.

SIXTEENTH EMBODIMENT OF THE INVENTION (FIGS. 43-45)

The syringe according to the invention is here marked 160 in its entirety. This comprises a cylindrical tubular body 161 with a coaxial, trunk-conical, integral hollow beak 162, forming a needle-holder head. A plunger 163 is inserted, in a tight and axially-sliding fashion, into this tubular body 161.

At its free axial end zone, the beak 162 displays a circumferential lip 162.1 delineating a frontal axial mouth 162.2. A retractable bushing 164 for forced mounting of a coaxial empty needle 165 is inserted into this beak, coaxially and form-coupled for part of its axial length, but not by forcing. Needle 165 extends axially from the bushing through frontal mouth 162.2 of the needle-holder head, and communicates, in bushing 164, with an axial through hole 164.1, emerging onto the dorsal face 164.2 of the bushing, facing plunger 163.

Bushing 164 extends with its free axial end zone 164.3 into the space for tubular body 161, out of contact with the wall thereof. Axial end zone 164.3 is conically tapering in a direction towards plunger 163, and along its free circumferential edge, it displays an annular coupling projection 164.4, directed radially towards the exterior of bushing 164 and likewise displaying a profile conically tapering towards plunger 163. In addition, this free end zone 164.3 is partially inserted into a cylindrical retaining ring 166, arranged in tubular body 161 in sliding contact with the cylindrical wall thereof. Retaining ring 166 is distanced from needle-holder head 162. This has an internal diameter greater than the maximum overall cross-sectional dimension of bushing 164, and is made integral with bushing body 164 by means of thin breaking joint tongues 166.1 (FIG. 45). This ring 166 extends towards plunger 163 beyond annular projection 164.4 of bushing 164. Upon assembly, this retaining ring 166 is axially forced to overshoot the minute, elastically pliable retaining projections 161.1, jutting out from the wall of tubular body 161 into the space thereof and capable of resisting the axial withdrawal of ring 166. These projections 161.1, in addition to retaining ring 166, constitute the means for retaining needle 165 in the use position. In fact, with ring 166, bushing 164 is also prevented from withdrawing in an axial direction by retaining means 161.1.

Plunger 163 frontally carries an integral axial head 163.1, set against bushing 164, and constituting the means for disengaging the retaining means 167 from the bushing. Disengagement head 163.1 has a smaller diameter than the body of syringe 163, but larger than the internal diameter of retaining ring 166, thus enabling this ring to be engaged. In this way, this head 163.1 can be forced in an axial direction against retaining ring 166 until joint tongues 166.1 are caused to break. In such a state, bushing 164 may be axially retracted from the beak 162 of syringe 160.

On the frontal face of disengagement head 163.1, there is formed an axial coupling cavity 163.2, substantially trunk-conical, which displays an annular coupling band 163.3, projecting radially towards the interior of said cavity at the free edge thereof. This coupling cavity 163.2 is shaped and arranged to join the free end of bushing 164 having annular projection 164.4, with the annular coupling band 163.3 being axially forced to override annular projection 164.4 by elastic release. Annular coupling projection 164.4 of bushing 164, and axial cavity 163.2 with coupling band 163.3 of head 163.1 integral to plunger 163, constitute the means for inseparable coupling between bushing 164 and plunger 163, in step with the disengagement of retaining means 167 from the bushing.

Otherwise, please refer to the explanation for syringe 10 (FIGS. 1-6).

SEVENTEENTH EMBODIMENT OF THE INVENTION (FIGS. 32-33)

The syringe according to the invention is here marked 170 in its entirety. This comprises a cylindrical tubular syringe body 171 having an integral needle-holder head 172, coaxial and also cylindrical, but of smaller diameter. At its free axial end zone, this needle-holder head 172 displays a circumferential lip 172.1.

A cylindrical tubular capsule 173 is coaxially fitted onto this head 172, for part of the length thereof, and is prevented from shifting in an axial direction away from that head, by means of engaging the circumferential lip 172.1 of head 172 through elastic release inside a matching circumferential groove provided on the external face of capsule 173.

A retractable bushing, marked 174 in its entirety, for mounting a coaxial empty syringe needle 175, is tightly housed in capsule 173, coaxially and form-coupled for part of its axial extension, but not by forcing. Bushing 174 comprises a cylindrical tubular jacket 174.1, coupled into capsule 173 with its smaller-diameter section 174.2, and housed in the remaining portion of head 172 by means of its larger-diameter section 174.3, axially-extending into the space for the syringe body 171, out of contact with the wall thereof. An annular shoulder 174.4 is formed in the splicing zone between these cylindrical sections of jacket 174.1. An annular elastic sealing gasket 173.1 is interposed between the shoulder of jacket 174.1 and capsule 173.

The mouth of larger-diameter section 174.3 of jacket 174.1 is closed by means of a base 176, e.g. made of plastic material, forced into the mouth itself. In addition, at its free axial end zone delineating this mouth, this larger-diameter section 174.3 of jacket 174.1 displays an annular coupling projection 174.5, directed radially towards the exterior of the jacket.

A needle-holder column 177 for forced mounting of empty syringe needle 175 inside its axial through hole 177.1, is housed, axially sliding, in tubular jacket 174.1. Needle-holder column 177 displays cylindrical body 177.2 having a diameter corresponding to the internal diameter of the smaller-diameter section 174.2 of jacket 174.1, to be partially received there by axial sliding. At its axial end zone proximal to base 176, this cylindrical body carries an integral annular collar 177.3, engaged in a tight and axially-sliding fashion against the wall of the larger-diameter cylindrical section 174.3 of jacket 174.1.

A helicoidal compression spring 179 is housed in the abovementioned larger-diameter cylindrical section 174.3 of jacket 174.1, coaxially to the cylindrical section 177.2 of column 177, and is interposed, like a return spring, between annular collar 177.3 of needle-holder column 177 and annular shoulder 174.4 of jacket 174.1. This spring normally keeps elastically stressed the needle-holder column 177 in tight contact against base 176 by means of its annular collar 177.3.

From cylindrical body 177.2 of column 177 there extends, beyond annular projection 177.3, an integral, axial handle 177.4 received passing and sliding through a pertinent axial hole in base 176 and normally projecting into the space of syringe body 171.

At its axial end zone distal from the handle 177.4, the cylindrical body 177.2 of column 177 further carries a reduced-diameter, integral, axial stem 177.5, in turn supporting an integral, coaxial actuating head 177.6.

This actuating head 177.6 displays a substantially cylindrical section 177.7 having a diameter a little smaller than the internal diameter 174.2 of jacket 174.1, and wherefrom there extends, towards the outside of said jacket, a trunk-conical beak having coaxial free end 177.8, accommodating needle 175. (This beak 177.8 is provided for the purpose of coupling a conventional needle and syringe needle-holder, in the absence of needle 175). At the same time, cylindrical section 177.7 of actuating head 177.6 is spliced to axial stem 177.5 by means of section 177.9 conically tapering in a direction towards the handle 177.4. In the arrangement of the needle-holder column 177 with respect to jacket 174.1., in which its annular collar 177.3 is elastically maintained in tight contact against base 176, the cylindrical section 177.7 of actuating head 177.6 is arranged, within jacket 174.1, in the proximity of the free axial end zone, forming a frontal aperture, of the smaller-diameter section 174.2 of the same jacket.

In the proximity of this aperture zone of the smaller-diameter section 174.2 of jacket 174.1, two diametrically opposed through holes 174.6 are therein formed. With these holes 174.6 in jacket 174.1, there coincides a circumferential groove 173.2 formed on the inner face of capsule 173. In bushing 174, at through holes 174.6, there are arranged pertinent retaining balls 174.7, resting against the lateral surface of actuating head 177.6. In the abovementioned relative arrangement of needle-holder head 177 and jacket 174.1, in which the column's annular collar 177.3 is elastically maintained in tight contact against base 176, the abovementioned retaining balls 174.7 rest against the surface of the cylindrical section 177.7 of the actuating head. This causes them to partially protrude via the through holes 174.6 of jacket 174.1, and thus cause's partial engagement of capsule 173 within groove 173.2. In such a position, the retaining balls 174.7 prevent the axial passage of the bushing 174 with respect to capsule 173. This ensures that needle 175 is in a secure operating position.

A plunger 178 is housed, in a tight and axially-sliding fashion, in the tubular body of syringe 171. On the frontal face of plunger 178, turned towards bushing 174, there is formed a substantially cylindrical, axial coupling cavity 178.1 displaying an annular coupling band 178.2, projecting radially towards the interior of the free edge of said cavity. Coupling cavity 178.1 is shaped and arranged to join the axial end zone—with base 176—of the larger-diameter section of jacket 174.1 of bushing 174, with annular coupling band 178.2 being forced in an axial direction to override annular coupling projection 174.5 of jacket 174.1 by elastic release. Annular coupling projection 174.5 of jacket 174.1, and axial coupling cavity 178.1 with coupling band 178.2 of plunger 178, constitute the means for inseparable coupling between bushing 174 and plunger 178. This inseparable coupling takes place in step with the action of disengaging the retaining balls 174.6 from groove 173.2 of capsule 173. In fact, the plunger 178, in its advancement in an axial direction towards bushing 174, engages handle 177.4 of needle-holder column 177, causing pertinent axial sliding of said column in jacket 174.1, at odds with the elastic action of spring 179. The length of the axial stroke of handle 177.4—and thus of column 177 in its entirety—under thrust action by plunger 178, is chosen in such a way that, once handle 177.4 has completely re-entered base 176 (FIG. 33), the actuating head 177.6 is found with its conically tapering section 177.9 at the retaining balls 174.7. These retaining balls 174.7 thus rest against conically tapering section 177.9, are positioned inside the jacket 174.1, and release the groove 173.2 of capsule 173. In such a state, bushing 174 may be axially retracted from capsule 173.

Otherwise, please refer to the explanation for syringe 10 (FIGS. 1-6).

OPERATION OF SYRINGE 10 (FIGS. 1-6 AND 46, 47)

FIG. 2 shows how syringe 10 is presented for use, after removing the cap for protecting needle 17 (cap not illustrated).

Stage for automatic suction of injectable liquid into syringe 10

We immerse needle 17 into the liquid to be sucked in. We rotate cap 10.2 by substantially ninety degrees, in the direction indicated by arrow F in FIG. 2, disengaging it from flange 11.2 of syringe body 11. We remove cap 10.2, while plunger 13 is automatically carried back through axial sliding in the direction indicated by arrow F1 in FIG. 46, towards axial end zone 11.1 of syringe body 11, under the elastic thrust action exerted by return spring 10.1. The liquid is thus automatically sucked into syringe 10.

Preferably, the elastic force of the return spring 10.1 will be calibrated in such a way as to obtain the automatic axial retraction of plunger 13 not far beyond the transverse center line of syringe body on condition that the approximate midway length of the syringe body can ultimately house bushing 16 and needle 17, retracted in a manner integral with said plunger, as shall become more apparent further on. In addition, it may prove beneficial to make provision for the terminal stretch of the suction stroke for plunger 13 to be manually driven, thereby distancing the plunger shaft's actuating foot 13.3 from the corresponding axial end of return spring 10.1. This device is helpful, e.g., in enabling the bleeding of any air sucked in with the injectable liquid.

Stage for injecting the liquid

In a conventional manner by thrust in an axial direction, in the direction indicated by arrow F2 in FIG. 3, we manually bear down upon the plunger shaft's actuating foot 13.3, until we bring the disengagement means 19 integral with plunger 13 up against the retaining means 18 integral with capsule 14. Substantially all the liquid is thereby injected out of syringe 10, while spring 10.1 is elastically loaded in order then to act elastically in the opposite direction in the manner of a return spring.

Stage for automatic axial retraction of bushing 16 bearing needle 17, in a manner integral with plunger 13

By continuing the abovementioned axial thrust action in the direction of arrow F2 (FIG. 3), we cause spreader collar 19.1 of disengagement means 19 to be engaged between and against retaining teeth 18.2 of retaining means 18. By forcing collar 19.1 by axial thrust, softly and in a gradual manner, we cause retaining arms 18.1 bearing teeth 18.2 to spread elastically towards the wall of the needle-holder head. In fact, these teeth 18.2 engage the external surface of the collar 19.1, upon which they make a sliding contact, while collar 19.1 externally strikes the free axial end zone of additional cylindrical section 16.4 of bushing 16 (FIG. 5).

The abovementioned action is performed in step with the axial penetration of coupling head 13.4, integral to plunger 13, into coupling cavity 16.5 of bushing 16. This penetration achieves the inseparable coupling of plunger 13 with bushing 16, upon juxtaposition between the bushing's dorsal face 16.6 and the plunger's frontal face 13.5. Thereby completed is the forced expulsion of the liquid to be injected through empty needle 17. Further axial advancement by plunger 13 is prevented, and any residual force applied to plunger 13 by axial thrusting in the direction of arrow F2 is partially absorbed by annular elastic gasket 15, which acts like a spring.

In such a state, bushing 16 may be axially retracted from capsule 14, which is instead designed to remain in place, being bound to needle-holder head 12.

By releasing the plunger shaft's actuating foot 13.3, capsule 16 and needle 17 are automatically retracted into syringe body 11 in the axial direction indicated by arrow F3 in FIG. 47, in a manner integral with plunger 13, returned by means of spring 10.1 towards axial end 11.1 of syringe body 11. The teeth 18.2 of retaining arms 18.1 do not interfere with this retraction of the bushing 16, as these teeth are maintained in sliding contact first with spreader ring 19.1 and then with the lateral surface of bushing 16.

In this way, needle 17 is automatically retracted into a protected position in syringe body 11, regardless of the operator's intentions. Syringe 10 may be disposed of, without risk of injury and contamination caused by syringe needle 17.

Furthermore, syringe 10 cannot be reused.

Operation of the syringe according to the second thru fifteenth embodiments of the invention The above-described operation is repeated for the various embodiments of the invention: from the second to the fifteenth embodiment, with functional differences at the stage for automatic retraction of the bushing for mounting the needle, and the needle itself, into the syringe body, which will be self-evident on the basis of the foregoing descriptions and illustrations. We shall accordingly dispense with any further description.

With respect to the eleventh embodiment of the invention (FIGS. 38-39), it will be noted that syringe body 111 of syringe 110 may serve as a sealed phial, containing, for example, an injectable medication, or else as a sterile laboratory test-tube, onto which we then push needle-holder head 113 with capsule 14 and bushing 16 for mounting needle 17, and in whose plunger 112 the shaft 115 is engaged with a coaxially-fitted return spring 116.

Standardized attachment 111.1 for syringe body 111, makes it possible to connect up the same syringe body, with plunger 112 incorporated, in conjunction with other devices, serving as an injector.

Operation of syringe 160 (FIGS. 43-45)

This operation differs from the operation for syringe 10 just at the stage at which bushing 164 with needle 165 are axially retracted into syringe body 161, a stage that shall be described below.

At the stage of injection of the liquid contained in syringe 160, plunger 163 is axially driven to engage retaining ring 166 with its disengagement head 163.1. Continuation of the axial thrust action, transmitted to ring 166, causes joint tongues 166.1 to break. Bushing 164 is thus disengaged from retaining ring 166, and may thus be axially retracted from needle-holder head 162. Ring 166 is thus caused to advance in an axial direction towards needle-holder head 162 in a manner integral with plunger 163.

In step with this advancement, the coupling cavity 163.2 of the plunger's disengagement head 163.1 joins the free axial end zone of bushing 164, having annular coupling projection 164.4, while the annular coupling band 163.3, projecting into the same cavity, is axially forced to override annular coupling projection 164.4 of bushing 164, by elastic release. Thus is the inseparable coupling achieved between plunger 163 and bushing 164 for mounting empty needle 165.

Bushing 164 with needle 165 are axially retracted into syringe body 161 in a manner comparable to the explanation given for syringe 10. During its axial retraction, bushing 164 is passed through ring 166 which stays in place near needle-holder head 162.

Operation of syringe 170 (FIGS. 32–33)

This operation likewise differs from the operation for syringe 10 just at the stage at which bushing 174 with needle 175 are automatically retracted into syringe body 171. The operation of syringe 170 at this stage is self-evident from the description thereof given with reference to the seventeenth embodiment of the invention as described above, to which the reader is referred.

Without prejudice to the principle behind the invention, the details of execution and embodiments of the invention can of course be widely varied with respect to the descriptions and illustrations here given solely by way of example, and not intended to be restrictive, without thereby departing from the scope of the invention and hence from the scope of the present industrial patent right.

In this way, for example, the means of inseparable coupling between the plunger and the bushing for mounting the empty needle may alternatively be of the hook type, integral to one of these parts, and which can be inseparably thrust into a pierceable support, such as a facing rubber headpiece, integral to the other part; or else of the permanent magnet variety, integral to one of these parts, and cooperating with a ferromagnetic plate integral to the other part.

With reference to the seventeenth embodiment of the invention, as described above (FIGS. 32, 33), in syringe 170 the capsule 173 may be omitted, by suitably shaping the needle-holder head 172. In that case, the bushing for mounting the empty needle is tightly housed in the needle-holder head, with the possibility of retraction in an axial direction, while the means for retaining the empty needle in the use position (retaining balls), act upon the needle-holder head (in a groove therein), in a manner disengageable therefrom, in order to prevent the bushing from withdrawing in an axial direction.

At the same time, the means for retaining the empty needle in the use position may comprise just one retaining arm or tooth, or more than two retaining arms or teeth.

In addition, elastic means other than those illustrated and described herein may be used as means for automatically returning the plunger.

I claim:

1. A disposable safety syringe, containing a tubular syringe body with a needle-holder head integral to one of its axial end zones, wherefrom there axially extends an empty needle communicating, by means of a mounting bushing integral with said needle, with the cavity of the syringe body for the purpose of injecting liquids contained in said cavity, and further comprising a plunger, housed in said syringe body in a tight and axially-slidable fashion, and which can be slide-driven by means of a shaft, extending with one of its end zones outside the syringe body through an aperture in said body provided at its axial end zone opposite to the needle holder head, and also means for inseparable coupling between the empty needle and the above-mentioned plunger, by means of the said mounting bushing, achieving said coupling at the end of the stage for injecting the liquid contained in the syringe body, and means for automatically returning the plunger to a position retracted in an axial direction inside the syringe body, which means consist of a spring which is loaded by depression of the plunger during the stage for injecting the liquid contained in the syringe body and acts upon cessation of the manual action exerted on the plunger upon completion of the injection of liquid contained in the syringe body, as well as means for retaining the empty needle in the use position, which means are separate from and disengageably bind the bushing to the needle-holder head, in which the bushing is itself inserted in such a way that it can be retracted in an axial direction, and means of disengaging these retaining means, which disengaging means are integral with the plunger and are led thereby to contact the retaining means at the end of the stage for injecting the liquid contained in the syringe body, and disengage the bushing for mounting the empty needle to retaining means, characterized in that the above-mentioned means for automatically returning the plunger to a retracted position are separate from and independent of the empty needle and its mounting bushing before and during the stage for injecting the liquid contained in the syringe body and are connected with the empty needle and its mounting bushing, through the plunger and the means for inseparable coupling between the empty needle and the plunger, upon completion the stage for injecting the liquid contained in the syringe body, thereby ensuring that the bushing for mounting the empty needle can be retracted, in an axial direction, from the needle-holder head upon completion of the stage for injecting the liquid contained in the syringe body, substantially in step with the action for inseparable coupling between the plunger and the bushing for mounting the empty needle, in such a way that, upon completion of the stage for injecting the liquid, the plunger is automatically retracted, by the said automatic plunger return means, into the syringe body and, in a manner integral to and inseparable from the plunger, the empty needle and its mounting bushing are also automatically retracted into a safety position inside the syringe body, irrespective of the operator's intention.

2. Disposable safety syringe according to claim 1, characterized in that the needle-holder head (12; 22; 32; 71; 131; 152) is separated from and tightly inserted onto the syringe body (11; 21; 31; 72; 111), and consists of a cap for mounting the empty needle, in which are coaxially supported and tightly engaged the means for retaining the empty needle in the use position and the bushing for mounting the empty needle with the empty needle in the use position.

3. Disposable safety syringe according to claim 1, characterized in that the retaining means (18; 41; 63; 82; 93.3; 122) are integral to a capsule (14; 42; 62; 81; 93; 121), which houses, in a tight and axially retractable manner, the bushing (16; 61) for mounting the empty needle (17); in that the capsule is in turn tightly inserted and securely bound inside the needle-holder head (12; 92; 120.1) of the syringe (10; 40; 60; 80; 90; 120); and in that these retaining means act upon the bushing, in a manner disengageable therefrom, thus preventing the bushing from withdrawing in an axial direction.

4. Disposable safety syringe according to claim 1, characterized in that the retaining means (26; 36; 144; 151) are integral to the needle-holder head (22; 32; 142; 152), which houses, in a tight and axially retractable manner, the bushing (24; 34; 143; 153) for mounting the empty needle (25; 35) of the syringe (20; 30; 140; 150); and in that these retaining means act upon the bushing, in a manner disengageable therefrom, thus preventing the bushing from withdrawing in an axial direction.

5. Disposable safety syringe according to claim 1, characterized in that the retaining means (174.7) are carried by the bushing (174) for mounting the empty needle (175), which bushing is housed in a capsule (173) in a tight and axially retractable manner; in that the capsule is in its turn tightly inserted and securely bound into the needle-holder head (172) of the syringe (170); and in that the retaining means act upon the capsule, in a manner disengageable therefrom, thus preventing the withdrawal in an axial direction by this bushing for mounting the empty needle.

6. Disposable safety syringe according to claim 3, characterized in that the retaining means (18; 41; 63) comprise at least one retaining arm (18.1; 41.1; 63.1), extending from the capsule (14; 42; 62) and engaging the axial end zone of the bushing (16; 61) for mounting the empty needle (17) distal from said needle, thus keeping the bushing from withdrawing in an axial direction.

7. Disposable safety syringe according to claim 6, characterized in that the retaining means (18; 41; 63) comprise a pair of retaining arms (18.1; 41.1; 63.1) extending from the capsule (14; 42; 62) and forming a fork that can be engaged and elastically spread by the disengagement means (19; 65).

8. Disposable safety syringe according to claim 6, characterized in that at least one retaining arm (18.1; 41.1) is provided with at least one retaining tooth (18.2; 41.2) engaged against the dorsal face (16.6) of the bushing (16).

9. Disposable safety syringe according to claim 6, characterized in that at least one retaining arm (63.1) is provided with a retaining notch (63.2), in which there is engaged a corresponding annular projection (61.1) formed on the axial end zone of the bushing (61) distal from the empty needle (17).

10. Disposable safety syringe according to claim 3, characterized in that the retaining means (82; 93.3; 122) comprise at least one retaining tongue (82.1; 93.3; 122.1) extending from the capsule (81; 93; 121) towards the interior of said capsule and abutting, with its free end zone, against the dorsal wall (16.6) of the bushing (16), thus keeping the bushing from withdrawing in an axial direction.

11. Disposable safety syringe according to claim 4, characterized in that the retaining means (26; 36; 144; 151) comprise at least one retaining tooth (26.2; 36.1; 144.1; 151.2) integral to the needle-holder head (22; 32; 142; 152) and engaging the bushing (24; 34; 143; 153) for mounting the empty needle (25; 35), thus keeping the bushing from withdrawing in an axial direction.

12. Disposable safety syringe according to claim 4, characterized in that the retaining means (151) comprise at least one retaining arm (151.1; 151.3), extending from the needle-holder head (152) and engaging by one of its teeth (151.2) the axial end zone of the bushing (153) for mounting the empty needle (35) distal from the needle itself, thus keeping the bushing from withdrawing in an axial direction.

13. Disposable safety syringe according to claim 12, characterized in that the retaining means (151) comprise a pair of retaining arms (151.1, 151.3) extending from the needle-holder head (152) and forming a fork that can be engaged and elastically spread by the disengagement means (38).

14. Disposable safety syringe according to claim 4, characterized in that the retaining means (26) consist of a retaining ring (26.1), securely housed in a circumferential groove provided on the inner face of the needle-holder head (22) in a position directly upstream from the bushing (24), according to the direction of injection of the liquids in the syringe (20), and displaying a pair of diametrically opposed retaining teeth (26.2), and engaging the dorsal face (24.5) of the bushing (24) with their free end zone, the which bushing can be axially passed through said ring, once the retaining teeth (26.2) have been spread out towards the wall of the needle-holder head by the disengagement means (28).

15. Disposable safety syringe according to claim 1, characterized in that the retaining means (167) comprise a retaining ring (166) arranged in the tubular body (161) of the syringe (160) in sliding contact with the wall thereof and distanced from the needle-holder head (162) of said syringe; in that the retaining ring is rendered integral to the bushing (164) for mounting the empty needle (165) by means of thin breaking-joint tongues (166.1); and in that the retaining means (167) further comprise at least one retaining projection (161.1), jutting out from the wall of the tubular body (161) into the space thereof and opposing the axial withdrawal of the ring (166) and hence of the bushing (164), the which bushing may be axially passed through this ring once the joint tongues (166.1) have been broken by the disengagement means (163.1).

16. Disposable safety syringe according to claim 1, characterized in that the disengagement means comprise a spreader ring (146), which is interposed, in the tubular body (141) of the syringe (140), between the plunger (145) and the bushing (143) for mounting the empty needle, and which is arranged to freely slide in contact with the wall of the tubular syringe body (141) in a manner integral with the plunger in order to be readily engaged, by gradual axial forcing as a result of the axial advancement of the plunger, against at least one retaining tooth (144.1), in the manner of spreader mechanism; and that this spreader collar strikes, externally and for at least a portion of its axial length, the axial end zone (143.1) of the bushing (143) set against the plunger and which is extended into the syringe, or respectively into the capsule, out of contact with the wall thereof.

17. Disposable safety syringe according to claim 11, characterized in that, coinciding with at least one retaining tooth (144.1), the wall of the needle-holder head (142) is made significantly thinner by means of an external circumferential groove (141.1), the elastic pliability of which makes it easier to engage the disengagement means (146) against at least one retaining tooth (144.1).

18. Disposable safety syringe according to claims 1, characterized in that the disengagement means (19) comprise a rigid annular collar (19.1) extending from the frontal face (13.5) of the plunger (13) opposite the bushing (16) for mounting the empty needle, and capable of being readily engaged, by gradual axial forcing as a result of the axial advancement by the plunger, against at least one retaining tongue (82.1; 93.3; 122.1), penetrating into the capsule (81; 93; 121) in the manner of a spreader mechanism, until ultimately pushing back at least one tongue by elastic bending onto the peripheral outline of the capsule, with the collar striking, externally and for at least a portion of its axial length, the axial end zone of the bushing (16) set against the plunger, and that is extending into the capsule out of contact with the wall thereof.

19. Disposable safety syringe according to claim 15, characterized in that the disengagement means comprise a disengagement head (163.1) integral to the plunger (163) and set against the bushing (164), and that this disengagement head, as a result of the axial advancement of the plunger, is forced against the retaining ring (166), with which it interferes, thus causing the breakage of the tongues (166.1) for connecting the ring to the bushing (164).

20. Disposable safety syringe according to claim 1, characterized in that it displays a syringe body (111) bearing at one of its axial ends a threaded, cylindrical and tubular, standardized attachment (111.1), for engaging an added standardized needle-holder head (113) tightly and by means of screwing, or else for connecting up the syringe body with other devices to serve as an injector.

21. Disposable safety syringe according to claim 1, characterized in that it comprises a plunger shaft (115) that may be disengaged from the plunger (112), and arranged through and slide-driven into a hole (114.2) in a base (114), engaged at the axial end of the syringe body (11) opposite to the axial end displaying the needle-holder head (113), with this base (114) preventing the plunger from being extracted from the syringe body, in such a way that this syringe body may also be used e.g. as a phial for injectable medications, or as a sterile laboratory test-tube.

22. Disposable safety syringe according to claim 2, characterized in that the needle-holder head displays a hollow syringe neck (131.2) out of axial alignment; and in that the bushing (132) for mounting the empty needle displays an axial end section (132.1) accommodating this empty needle, coupled into the neck of the syringe and out of axial alignment with the remaining portion of the same bushing (132.2, 132.3), which is coaxial with the body (31) of the syringe.

23. Disposable safety syringe according to claim 1, characterized in that the bushing (174) displays a trunk-conical beak having a free end (177.8) provided for the purpose of coupling a conventional empty needle and syringe needle-holder.

24. Disposable safety syringe according to claim 1, displaying a syringe body (91; 120.3) with an integral neck (92; 120.1) of the conventional type, characterized in that in this syringe body there are inserted a capsule (93; 121) having a cylindrical shell (93.1; 121.1) for housing a bushing (16) for mounting an empty needle (17) according to claims 3 and 11, in addition to disengagement means (19) according to claim 21; and in that at one of its axial ends, this capsule carries an integral tube (93.2; 121.1), through which there extends the empty needle (17); tightly engaged by forcing into the neck of the syringe (92; 120.1).

25. Disposable safety syringe according to claim 1, comprising a rigid cap for safety and protection, fitted onto that portion of the plunger shaft that extends beyond the body of the syringe, and removably anchored to the same syringe body, characterized in that the said cap (10.2) is adapted to maintain the plunger in an axially advanced position up to being in proximity of the bushing for mounting the empty needle, without contact with said bushing, thereby resulting in preloading of these return means, which bring about the automatic axial retraction of the plunger and thus cause the liquid to be automatically sucked up into the syringe, as soon as the cap has been removed.

26. Disposable safety syringe according to claim 1, characterized in that the inseparable coupling means comprise a permanent magnet or magnets integral to the plunger, or to the bushing for mounting the empty needle, and a plate or plates made of ferromagnetic material integral to said bushing or said plunger opposing said magnet or magnets.

* * * * *

UNITED STATES PATENT AND TRADEMARK OFFICE
CERTIFICATE OF CORRECTION

PATENT NO. : 5,112,316

DATED : May 12, 1992

INVENTOR(S) : Aldo VENTURINI

It is certified that error appears in the above-identified patent and that said Letters Patent is hereby corrected as shown below:

On the Title page,
item [76] under Inventor, delete "Via Orbetello N. 176,I-10148 Turin, Italy" and insert therefor --Via Don P. Minetti No. 73 10017 MONTANARO (TORINO) ITALY On the Title page, item [57]
in the Abstract, col. 2, line 10, delete "diseng gaing" and insert therefor --disengaging--.

claim 18, col. 24, line 62, delete "claims" and insert therefor ---claim---.

Signed and Sealed this

Twenty-eighth Day of September, 1993

Attest:

BRUCE LEHMAN

Attesting Officer        Commissioner of Patents and Trademarks